United States Patent
Grégoire et al.

(10) Patent No.: US 6,372,690 B1
(45) Date of Patent: Apr. 16, 2002

(54) FOLIAR SALINE SPRAY SOLUTION FOR SELECTIVE CONTROL OF NOXIOUS WEEDS

(75) Inventors: André Grégoire, Bois Briand; Gérard Lupien, Laval; Alan K. Watson, Ste-Anne-de-Bellevue; Antonio DiTommaso, Montréal, all of (CA)

(73) Assignee: McGill University, Montreal (CA)

( * ) Notice: Subject to any disclaimer, the term of this patent is extended or adjusted under 35 U.S.C. 154(b) by 0 days.

(21) Appl. No.: 09/046,094

(22) Filed: Mar. 23, 1998

(51) Int. Cl.$^7$ ............................................. A01N 59/08

(52) U.S. Cl. ................................................. 504/116.1

(58) Field of Search ............................... 504/187, 188, 504/116.1

(56) References Cited

U.S. PATENT DOCUMENTS

| | | | |
|---|---|---|---|
| 1,354,043 A | 9/1920 | Kramer | 504/188 |
| 5,330,964 A | 7/1994 | Alesi | 504/119 |

FOREIGN PATENT DOCUMENTS

| | | |
|---|---|---|
| CA | 2171254 | 3/1996 |

OTHER PUBLICATIONS

Stock et al. "Activation of the foliar uptake of two water-soluble compounds by alcohol polyoxyethylene surfactants". Chapter 13 in Adjuvants for Agrichemicals. Chester L. Foy, ed. CRC Press. pp. 159–167, 1992.*

Durant, Will. The Story of Civilization: Part III. Caesar and Christ. NY:Simon and Schuster. p. 107, 1944.*

Josephus, Flavius. The Wars of the Jews. Book VI. 4–5. Cited at http://www.geocities.com/Heartland/Valley/9211/holycity.html, AD 75.*

The Washington Times. "Bush backs Giuliani's stance against Brooklyn art exhbit", p. A3, Oct. 1999.*

Frear, *Chemistry of Pesticides*, 3rd ed. p. 401, 1955.

Koen Van Keer et al., Highland Farming: Soil and the Future?, Soil Fertility Conservation Project, Maejo University, Chiangmai, 1995.

* cited by examiner

Primary Examiner—S. Mark Clardy
(74) Attorney, Agent, or Firm—Klauber & Jackson

(57) ABSTRACT

The invention relates to a foliar saline spray solution for selective control of noxious weeds such as ragweed, poison ivy, dandelion, clover, bedstraw, wild parsley, millet, thistle, English daisy, plantain, ground-ivy, and knotweed. The invention also relates to a method for selective control of noxious weeds. In accordance with a preferred embodiment of the present invention, the solution comprises 8% to 12% weight to volume of a specific salt such as sodium chloride. The solution may further comprise an adjuvant such as a non-ionic surfactant.

6 Claims, 2 Drawing Sheets

FOLIAR SALINE SPRAY SOLUTION FOR SELECTIVE CONTROL OF NOXIOUS WEEDS

BACKGROUND OF THE INVENTION (a) Field of the Invention

The invention relates to a foliar saline spray solution for selective control of noxious weeds such as ragweed, poison ivy, dandelion, clover, bedstraw, wild parsley, millet, thistle, English daisy, plantain, ground-ivy and knotweed. The invention also relates to a method for selective control of noxious weeds.

(b) Description of Prior Art

There are many known herbicidal solutions for controlling vegetation. Some herbicidal solutions are selective, such as to control broad leaf weeds growing among grass, while others control a wider range of plant species. Some herbicidal solutions act to control vegetation when the active ingredient of the herbicidal composition comes into contact with the leaves of the plant, while others saturate the soil around the plant's roots and are subsequently absorbed by the roots.

A major drawback of many of the known herbicidal compositions is that they are not only toxic to the unwanted vegetation, but are also hazardous to man, the environment, and the wildlife. For instance, the user of a toxic herbicidal composition should be concerned with direct contact of the active ingredient of the herbicidal composition with the skin or eyes, and with vapors emitted by the herbicidal composition itself or the spraying thereof, inhaled into the lungs. Also of concern is the longevity of the herbicide residues remaining active in the soil which creates a potential for run off of the toxic herbicidal composition into the ground water. Many of the active ingredients used in herbicidal composition are known carcinogens.

Another drawback of the herbicidal composition of the prior art is that most compositions need to contain many active ingredients to ensure a broad spectrum of action.

Herbicidal compositions containing a non toxic active ingredient are known. U.S. Pat. No. 1,354,043 (Kramer) describe a herbicidal composition containing Lye, slack coal, saltpeter, and salt in specific proportion. This composition is described as a "poison" and the author suggests allowing a few weeks after the use of the poison for passing out to the soil.

Frear (Chemistry of Pesticides 3rd ed. p. 401, 1955) discloses that sodium chloride may be used as a herbicide but will kill all types of vegetation, without any selection.

U.S. Pat. No. 5,330,964 (Alesi) discloses a method of controlling low lying vegetation by providing and applying sodium bicarbonate on the vegetation so that the bicarbonate accumulate and forms a layer of between ⅛ to ¼ inch of thickness.

It would be highly desirable to be provided with a non-toxic foliar spray solution for selective control of noxious weeds.

It would also be highly desirable to be provided with a simple, yet inexpensive, foliar saline spray solution which is effective against undesirable weeds but which is non-toxic for the environment, the soil, mankind or the wildlife.

SUMMARY OF THE INVENTION

One aim of the present invention is to provide a non-toxic foliar spray solution for selective control of noxious weeds.

Another aim of the present invention is to provide a simple, yet inexpensive, foliar saline spray solution which is effective against undesirable weeds but which is non-toxic for the environment, the soil, mankind or the wildlife.

In accordance with the present invention there is provided a foliar saline spray solution for selective control of noxious weeds. The solution consists of 8% to less than 10% and most preferably 12%, weight to volume of at least one salt. The salt is preferably in a soluble form.

In a second embodiment, the solution consists of 8% to 20%, weight to volume, of at least one salt in combination with at least one adjuvant.

Also in accordance with the present invention, there is provided a method for selective control of noxious weeds, comprising contacting weeds with a growth inhibiting amount of a solution as defined above.

DETAILED DESCRIPTION OF THE INVENTION

Figure 1:
FIG. 1 illustrates the effects of a preferred embodiment of the foliar saline spray solution of the present invention on ragweed.

The foliar saline spray solution of the present invention comprises from 8% to 20% weight to volume (W/V) of salt in an aqueous solution, more preferably 8% to 12%, and most preferably 12%. A concentration of salt beyond the concentration in accordance with the present invention may result in inefficient solution when the concentration is lower than 8% W/V or may not be selective and kill grass or plants when the concentration is higher than 20% W/V.

If a low concentration of sodium chloride, such as 8% W/V, is used over a one-year period, several treatments may be required. However, one to three treatments are generally sufficient. A higher concentration, such as 20%, will normally require only a single treatment, over one growing season.

The salt is preferably selected from the group consisting of aluminum chloride, ammonium phosphate monobasic, calcium chloride dihydrate, calcium chloride hexahydrate, calcium chloride anhydrous, calcium hypochlorite, calcium nitrate tetrahydrate, decansulphonic sodium acid salt, ethylene diamine tetraacetic acid disodium (EDTA); ethylene diamine tetraacetic acid tetrasodium (EDTA), ferric chloride hexahydrate, ferric chloride, ferric nitrate nonahydrate, ferrous chloride tetrahydrate, hepes sodium salt, iodine chloride, lithium chloride, magnesium chloride hexahydrate, magnesium nitrate, manganese chloride, 1-pentanesulphonic acid sodium salt, potassium chloride, potassium nitrate, potassium nitrite, sodium acetate anhydrous; sodium acetate trihydrate, sodium azide, sodium β-glycerophosphate, sodium benzoate, sodium bicarbonate, sodium bisulphite, sodium borate decahydrate, sodium borohydride, sodium bromide, sodium carbonate anhydrous, sodium carbonate decahydrous, sodium carbonate monohydrous, sodium chloride, sodium chlorite, sodium iodide, sodium nitrate, sodium nitrite, sodium silicate, sodium sulfate, sodium sulfite, sodium tripolyphosphate, sorbic acid, zinc chloride and zinc nitrate hexahydrate. Since some salts may have a lower solubility, the solution in accordance with a preferred embodiment of the invention may comprise a solubilizing agent.

In accordance with one embodiment of the invention, the solution may further comprises at least one adjuvant selected from the group consisting of ACCUTROL™ spray adjuvant, ACTIPRON, AGRAL™ 90 (non-ionic surfactant), AG-SURF (non-ionic surfactant), AL 821, AL 826, AL 1399, ammonium sulfate, ALIPAL™ CO (Series non-ionic surfactants), AMIGO™ (surfactant), ASSIST™ oil concentrate (mineral oil surfactant), ATPLUS™ 411 F, ATPLUS™ 449, ATPLUS™ 555, AMWAY™ spray adjuvant, ATRAOIL™ concentrate, BCI 007, BESTLINE, BIO-FILM™, BIO-VEG™, BIVERT™ HCE, BIVERT™ PH, BIVERT™ TDN, Bob Chambers surfactant wetting agent, CANPLUS™ 411 (mineral oil surfactant), CD 351, CD 352, CD 353A, CHARGE™ mineral oil surfactant, CHEMPAR M, CHIPMAN corn oil concentrate, CITOWETT™ PLUS (nonionic surfactant), COMPANION™ (non-ionic surfactant), CONTROL™ OIL, CO-OP™ SURFACTANT, CO-OP™ emulsifiable spray oil (mineral oil), ENHANCE™ (cationic and non-ionic surfactant), ESSO-BAYOL 90, ETKOHEM, EV crop oil, FAIRMOUNT SURFACTANT wetting agent, FRIGATE™ (cationic surfactant), GENAPOL™ X-060, GENAPOL™ X-080, GENOM-OLL™ 100, GREEN CROSS™ adjuvant T, GREEN CROSS™ booster plus, IN 291, IN 292, IPCO™ oil concentrate (mineral oil), KANCEL™ spray additive liquid, KOMBAT™ NO.1, KORN oil (mineral oil), KORN oil concentrate (mineral oil surfactant), LATER'S SURFACTANT, LO-DRIFT™, low foam additive, MARASPERSE N-22 (non-ionic surfactants), MERGE™ (surfactant), MULTIFILM, NACCONOL™ 88SA (non-ionic surfactant), NALCOTROL™, POLYFON™ O (non-ionic surfactant), R 25788, R 33865, RAPE oil, REGULAID, RENEX™ 36, SIDE KICK, SIPON™ ES (non-ionic surfactant), SPRAYCO premium mineral oil (mineral oil), SPAYCO oil concentrate (mineral oil/surfactant), soybean oil, sorbitol, SUPERIOR oil concentrate (mineral oil/surfactant), SUPER SPREADER STICKER (nonionic surfactant spreader sticker), SURF™ 92 (non-ionic surfactant), SURFACTANT wk, Surfel, SYL-GARD™ 309 (non-ionic surfactant), TRITON™ AF adjuvant foamer, TRITON™ B1956 spreader sticker, TRITON™ CS 7 spreader sticker, TRITON™ X-100 (non-ionic surfactant), TRITON™ X-114, TRITON™ XA special spray adjuvant (non-ionic surfactant), TRITON™ XA spray adjuvant, TRITON™ XR, TURBOCHARGE™ (mineral oil), TWEEN™ 20 (non-ionic surfactants), TWEEN™ 40, TWEEN™ 60, TWEEN™ 80, vegetable oils (such as corn, soybean, flax, or cottonweed) (spreaders and stickers), and XA oil (mineral oil surfactant). Preferably the adjuvant is CITOWETT™ PLUS or AGRAL™ 90.

The adjuvant, when added to the solution of the present invention, is preferably present in concentration of 0.25% to 1% weight to volume.

The solution of the present invention is used for inhibiting the growth of a broad-leaved plant, such as ragweed, poison ivy, dandelion, clover, bedstraw, wild parsnip, millet, thistle, English daisy, plantain, ground-ivy, and knotweed.

In accordance with one embodiment of the invention, from 0.1 to 0.3 liter of a solution comprising from 80 to 120 grams of sodium chloride per 1000 grams of water, sprayed per square meter of land (1000 l/ha), has been found most effective for areas containing rather large, mature plants (>25 cm in height for example), as one would find at the end of August. Of course, if spraying occurs early after the first appearance of the plants, such as in June when ragweed plants are small (10–15 cm in height), then less volume is required for effective control.

The most preferred salt uses in accordance with the present invention is sodium chloride. Sodium chloride is inexpensive and readily available.

An adjuvant may also be used in the solution of the present invention. The adjuvants suitable for the present invention are the following: ACCUTROL™ spray adjuvant, ACTIPRON, AGRAL™ 90 (non-ionic surfactant), AG-SURF (non-ionic surfactant), AL 821, AL 826, AL 1399, ammonium sulfate, ALIPAL™ CO (Series non-ionic surfactants), AMIGO™ (surfactant), ASSIST™ oil concentrate (mineral oil surfactant), ATPLUS™ 411 F, ATPLUS™ 449, ATPLUS™ 555, AMWAY™ spray adjuvant, ATRAOIL™ concentrate, BCI 007, BESTLINE, BIO-FILM™, BIO-VEG™, BIVERT™ HCE, BIVERT™ PH, BIVERT™ TDN, Bob Chambers surfactant wetting agent, CANPLUS™ 411 (mineral oil surfactant), CD 351, CD 352, CD 353A, CHARGE™ mineral oil surfactant, CHEMPAR M, CHIPMAN corn oil concentrate, CITOWETT™ PLUS (nonionic surfactant), COMPANION™ (non-ionic surfactant), CONTROL™ OIL, CO-OP™ SURFACTANT, CO-OP™ emulsifiable spray oil (mineral oil), ENHANCE™ (cationic and non-ionic surfactant), ESSO-BAYOL 90, ETKOHEM, EV crop oil, FAIRMOUNT SURFACTANT wetting agent, FRIGATE™ (cationic surfactant), GENAPOL™ X-060, GENAPOL™ X-080, GENOM-OLL™ 100, GREEN CROSS™ adjuvant T, GREEN CROSS™ booster plus, IN 291, IN 292, IPCO™ oil concentrate (mineral oil), KANCEL™ spray additive liquid, KOMBAT™ NO.1, KORN oil (mineral oil), KORN oil concentrate (mineral oil surfactant), LATER'S SURFACTANT, LO-DRIFT™, low foam additive, MARASPERSE N-22 (non-ionic surfactants), MERGE™ (surfactant), MULTIFILM, NACCONOL™ 88SA (non-ionic surfactant), NALCOTROL™, POLYFON™ O (non-ionic surfactant), R 25788, R 33865, RAPE oil, REGULAID, RENEX™ 36, SIDE KICK, SIPON™ ES (non-ionic surfactant), SPRAYCO premium mineral oil (mineral oil), SPAYCO oil concentrate (mineral oil/surfactant), soybean oil, sorbitol, SUPERIOR oil concentrate (mineral oil/surfactant), SUPER SPREADER STICKER (nonionic surfactant spreader sticker), SURF™ 92 (non-ionic surfactant), SURFACTANT wk, Surfel, SYL-GARD™ 309 (non-ionic surfactant), TRITON™ AF adjuvant foamer, TRITON™ B1956 spreader sticker, TRITON™ CS 7 spreader sticker, TRITON™ X-100 (non-ionic surfactant), TRITON™ X-114, TRITON™ XA special spray adjuvant (non-ionic surfactant), TRITON™ XA spray adjuvant, TRITON™ XR, TURBOCHARGE™ (mineral oil), TWEEN™ 20 (non-ionic surfactants), TWEEN™ 40, TWEEN™ 60, TWEEN™ 80, vegetable oils (such as corn, soybean, flax, or cottonweed) (spreaders and stickers), and XA oil (mineral oil surfactant).

The concentrations of the adjuvant used is preferably of 0.25% to 1.0% weight to volume, and more preferably of 0.25% to 0.5% weight to volume.

The spraying of the solution of the present invention is conducted most effectively when the plant is relatively mature, but before the production of pollen. Accordingly, the spraying is preferably conducted two weeks from the first appearance of the plants until pollination, that is between the first week of July and the end of August, for Quebec or eastern Canada when the weather is warm. Most preferably, the spraying is conducted when the plants are shorter, such as on the first week of July, so that less volume is required. During such a period, only one treatment may be necessary, as the plant receiving the solution, generally becomes white or whitish, droops or withers, and dries out, in a matter of half a day. The plant desiccates but remains upright. After half a day, if the leaves of the plant so treated are not drooping or withering, and drying out, another treatment may immediately be applied.

The solution of the present invention may be used to preferably destroy ragweed, poison ivy, dandelion, clover, bedstraw, wild parsnip, millet, thistle, English daisy, plantain, ground-ivy and knotweed or any other broad-leaved species.

The optimal concentration within the range of 8 and 20% W/V of salt in solution and the conditions of application of the solution of the present invention may vary for plants from one species to another. Some plants from one species will react differently to a treatment with the salt solution than others. The reaction to the treatment with the solution of the present invention is thus different from one species to another. For instance, when spraying is conducted over poison ivy, the plant becomes brown and dries out after the treatment.

The typical curling and wilting of ragweed plant within 6 hours of applying a 12% NaCl solution is illustrated in FIG. 1.

Figure 2:
FIG. 2 illustrates the effects on ragweed 24 hours after applying the foliar saline spray solution in accordance with a preferred embodiment of the present invention.

FIG. 2 illustrates the typical drooping of ragweed staminate flowers and desiccation of leaves 24 hours following the spraying of a 12% NaCl solution. In sharp contrast, it is to be noted the healthy appearance of non-sprayed control ragweed plants (staminate flowers) at the far-right of the pictures.

Figure 3:
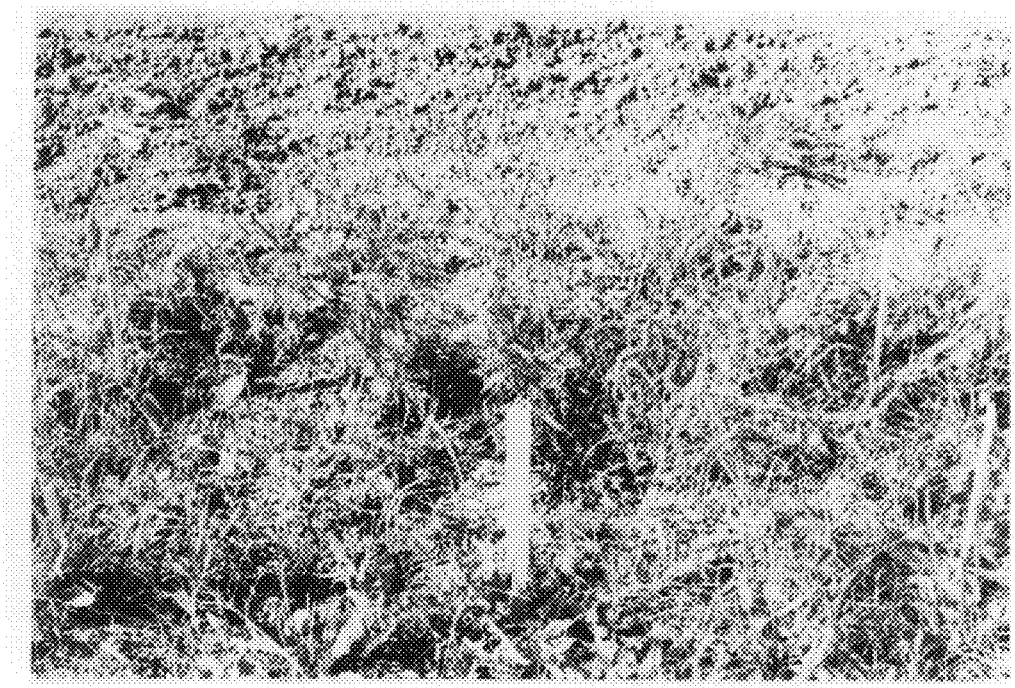
FIG. 3 illustrates ragweed plants not treated (left side of central yellow stake) or treated (right side of the central yellow stake) with the foliar saline spray solution in accordance with a preferred embodiment of the present invention.

FIG. 3 illustrates the effect of the solution of the present invention on healthy, non-sprayed ragweed plants of about 60 cm in height (left side of central yellow stake) and on desiccated ragweed plants 24 hours following application of a 12% NaCl solution (right side of the central yellow stake).

Figure 4:
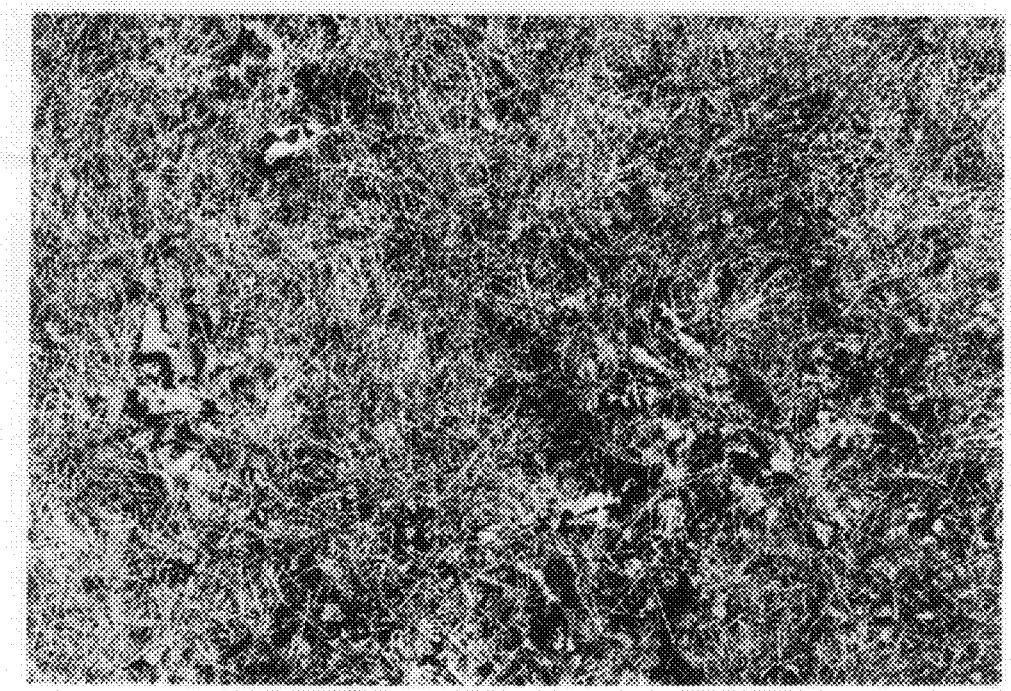
FIG. 4 illustrates the selective control of broad-leaved plantain in turf 24 hours following the application of a 12% NaCl solution.

The solution of the present invention has only a temporary effect on grass and does not contaminate the soil with toxic chemicals (FIG. 4). The solution used in accordance with the present invention has little effect on grass and other broad-leaf plant species treated. The solution is thus the answer to the public's demand for an environmentally friendly non-toxic or non-poison chemical, that still retains its selective herbicidal function.

The present invention will be more readily understood by referring to the following examples which are given to illustrate the invention rather than to limit its scope.

EXAMPLE I

Effects of Treatments of Ragweed with NaCl Solution

This experiment was conducted at McDonald Campus (McGill University, Ste-Anne-de-Bellevue, Quebec, Canada) on plots of short ragweed (8–16 inches), fully flowered in a cultivated field situation. The experiment was conducted as a randomized complete block design (RCBD) with three replicates.

Each plot has a surface of one (1) m². The sprayer used was a small compressed air sprayer with 210 Kpa of pressure and a T-Jet™ 8002 nozzle. The plots were sprayed Aug. 28, 1996 at 14:30 under a bright sunshine and a temperature of 28° C.

In all instances, the efficacy of the solution was evaluated 30 minutes, 2–4 hours, 16–24 hours, and 2–5 days after spraying. The efficacy of the solution was determined based on level of plant deterioration.

In this experiment, 18 different treatments (with three replicates) were subjected to the various plots. Table 1 summarizes the treatments applied to each plot.

TABLE 1

| Ingredients | Composition in aqueous solution % weight to volume |
|---|---|
| Weedy check | |
| NaCl | 8 |
| NaCl | 12 |
| NaCl | 16 |
| NaCl | 20 |
| NaCl + Agral ™ 90 | 8 + 0.25 |
| NaCl + Agral ™ 90 | 12 + 0.25 |
| NaCl + Agral ™ 90 | 16 + 0.25 |
| NaCl + Agral ™ 90 | 20 + 0.25 |
| NaCl + Agral ™ 90 | 8 + 0.5 |
| NaCl + Agral ™ 90 | 12 + 0.5 |
| NaCl + Agral ™ 90 | 16 + 0.5 |
| NaCl + Agral ™ 90 | 20 + 0.5 |
| NaCl + Agral ™ 90 | 8 + 1.0 |
| NaCl + Agral ™ 90 | 12 + 1.0 |
| NaCl + Agral ™ 90 | 16 + 1.0 |
| NaCl + Agral ™ 90 | 20 + 1.0 |
| $KNO_3$ | 12 |

The treatments were sprayed at a rate of 500 l/ha which translated to 50 ml/plot. No growth inhibiting activity was observed for any of the treatments 1 hour, 16 hours, 24 hours and 1 week after application. Since the success of this type of product depends on good coverage of the plant with spray solution, it was determined that the volume of material applied was not sufficient to thoroughly wet the leaves and other plant parts.

EXAMPLE 2

Determination of an Adequate Volume Sprayed

This experiment was conducted to determine if increasing the spray volume to the point where the plants were completely covered to the run-off stage would improve efficacy.

This experiment was conducted on plots within a fencerow of an agricultural field where ragweed plants had attained 12 to 20 inches in height, and were in full flower. The experiment was conducted as a completely randomized design (CRD) with three replicates.

Each plot has a surface of one (1) m². The sprayer used was a Hardi™ pack sprayer with Hardi™ nozzle and 200–220 kPa of pressure. The plots were sprayed Aug. 29, 1996 at 13:30 under a bright sunshine and a temperature of 29° C. The spray volume used was 1000 l/ha or 100 ml/m² plot.

In all instances, the efficacy of the solution was evaluated 30 minutes, 2–4 hrs, 16–24 hrs, and 2–5 days after spraying. The efficacy of the solution was determined based on level of plant deterioration.

In this experiment, 6 different treatments (having three replicates each) were subjected to the different plots. Table 2 summarizes the treatments applied to each plot.

TABLE 2

| Ingredients | Composition in aqueous solution % weight to volume |
|---|---|
| Weedy check | |
| NaCl | 8 |
| NaCl | 12 |
| NaCl | 16 |
| NaCl + Agral ™ 90 | 12 + 0.25 |
| NaCl + Agral ™ 90 | 12 + 0.5 |

Only 6 of the treatments from Experiment 1 were chosen for this purpose. At 30 minutes after spraying it was evident that the ragweed was reacting to the sprays. At all three concentrations of NaCl, the inflorescences were drooping. A white, salty residue on all sprayed areas of the plants was observed 2 hours after treatment. At 16 hours after application, the treated plants were brown. The treated ragweed was blackened and shriveled 3 days after application.

Observations made during and after application suggested that in order for the NaCl treatments to be effective, the solutions need to be applied copiously and evenly. Any part of a plant that was not well covered did not wilt until the rest of the plant had ceased functioning. If significantly large portions of the plant were not sprayed, then the plants often did not die. This experiments permitted the following conclusions: a) at least 1000 1/ha of spray solution must be applied to obtain adequate coverage. This volume also depends very much on the size and maturity of the ragweed being treated, i.e. it takes more time and more solution to cover a flowering 1 m tall plant than it does to treat a young, non-flowering, 4-leaf, 10 cm tall plant. Therefore, spray volume recommendations would have to be flexible; and, b) the addition of a surfactant seemed to decrease the amount of spray solution required to cover the area. The effect of the 12% solution+surfactant was slightly greater than 12% solution alone. There was no observed difference between the 0.25% and 0.5% rates of the surfactant Agral™ 90.

With regard to spray solution concentration, little difference between the 12% and 16% solution was visible at any time except 30 minutes after application. At this time, the plants sprayed with the 16% solution appeared to have wilted more quickly than those treated with 12%. In terms of overall efficacy, 12% would be sufficient. At a concentration of 8%, there was activity but it did not seem to be as effective as the 12% concentration at damaging the ragweed.

EXAMPLE 3

Assay with Other Non-Ionic Surfactants

This experiment was conducted to test another solution containing another non-ionic surfactant. The experiment was conducted on plots behind a beef barn complex, on ragweed of 6 to 10 inches in height, fully flowered, in a very hard and gravely soil, such as in a waste area situation. The experiment was conducted as a completely randomized design (CRD) with three replicates.

Each plot has a surface of one (1) m². The sprayer used was a small compressed air sprayer with 210 kPa pressure and a T-Jet™ 8002 nozzle. The plots were sprayed Sep. 3, 1996 at 10:00 a.m. under a bright sunshine and a temperature of 28° C. In all instances, the efficacy of the solution was evaluated 20–30 minutes, 2–4 hrs, 16–24 hrs, and 2–5 days after spraying. The efficacy of the solution was determined based on level of plant deterioration.

In this experiment, 14 different treatments were applied to the different plots (with three replicates/treatment). Table 3 summarizes the treatments applied to each plot.

TABLE 3

| Ingredients | Composition in aqueous solution % weight to volume |
|---|---|
| Weedy check | |
| NaCl | 8 |
| NaCl | 12 |
| NaCl | 16 |
| NaCl | 20 |
| NaCl + Agral ™ 90 | 8 + 0.25 |
| NaCl + Agral ™ 90 | 12 + 0.25 |
| NaCl + Agral ™ 90 | 16 + 0.25 |
| NaCl + Agral ™ 90 | 20 + 0.25 |
| NaCl + Citowett ™ | 8 + 0.25 |
| NaCl + Citawett ™ | 12 + 0.25 |
| NaCl + Citawett ™ | 16 + 0.25 |
| NaCl + Citawett ᴿᴹ | 20 + 0.25 |
| KNO₃ | 12 |

Once it had been determined that a surfactant could possibly increase efficacy of the NaCl at the same time as reducing the spray volume needed, another non-ionic surfactant, namely Citowett™, was introduced into the trials. All surfactants were applied at the rates usually recommended in the Ontario Guide to Chemical Weed Control (OMAFRA, 1997).

Using 16% or 20% NaCl did not visibly improve overall damage to the ragweed when compared with the effects of the 12% solution. The 8% solution alone was not as effective as the 12% solution. However, the addition of either Agral™ 90 or Citowett™ improved the efficacy of the 8% solution to almost that of the 12% solution applied alone. Agral™ 90 and Citowett™ only slightly increased the effectiveness of the 12% solution. The increased activity observed with the surfactants is likely due to the improvements in coverage obtained with these products.

KNO₃ was not as effective as any of the NaCl solutions.

At 4 days after application, plants which had shown symptoms of wilting, drooping and had had salt residues at 4 hours after spraying were blackened and completely inactive.

EXAMPLE 4

Determination of the Concentration of Salt used with or without Surfactants

This experiment was conducted on plot of tall ragweed (40–60 inches), fully flowered, in a cultivated field situation. The experiment was conducted as a completely randomized design (CRD) with three replicates.

Each plot has a surface of four (4) m². The sprayer used was a Hardi™ pack sprayer with 200–220 kPa pressure and T-Jet™ 8002 nozzle. The plots were sprayed Sep. 6, 1996 at 09:00 a.m. under a bright sunshine and a temperature of 26° C. In all instances, the efficacy of the solution was evaluated 30 minutes, 2–4 hrs, 16–24 hrs, and 2–5 days after spraying. The efficacy of the solution was determined based on level of plant deterioration.

In this experiment, 8 different treatments were applied to the different plots (with three replicates/treatment). Table 4 summarizes the treatments applied to each plot.

TABLE 4

| Ingredients | Composition in aqueous solution % weight to volume |
|---|---|
| Weedy check | |
| NaCl | 8 |
| NaCl | 12 |
| NaCl | 16 |
| NaCl | 20 |
| NaCl + Agral ™ 90 | 12 + 0.25 |
| NaCl + Citowett ™ | 12 + 0.25 |
| KNO₃ | 12 |

The results of this experiment were similar to those of Experiment 3. Again, the 12% solution applied without surfactant was as efficient as 16% or 20%. Control was slightly lower with the 8% solution but it is a viable rate, especially when used with a surfactant. Either Agral™ 90 or Citowett™ is useful in improving spray coverage and therefore overall control when used with 12% NaCl.

EXAMPLE 5

Optimization of the Concentration of Salt used with or without Surfactants

This experiment was conducted on plots having ragweed 4 to 6 inches tall, in flower, and which had been cut at least once, in a roadside situation. The experiment was conducted as a randomized complete block design (RCBD) with three replicates.

Each plot has a surface of four (4) m². The sprayer used was a small compressed air sprayer with 210 kPa pressure and T-Jet™ 8002 nozzle. The plots were sprayed Sep. 6, 1996 at 13:30, under a bright sunshine and a temperature of 29° C. In all instances, the efficacy of the solution was evaluated 30 minutes, 2–4 hrs, 16–24 hrs, and 2–5 days after spraying. The efficacy of the solution was determined based on level of plant deterioration.

In this experiment, 8 different treatments were applied to the different plots (with three replicates/treatment). Table 5 summarizes the treatments applied to each plot.

TABLE 5

| Ingredients | Composition in aqueous solution % weight to volume |
|---|---|
| Weedy check | |
| NaCl | 8 |
| NaCl | 12 |
| NaCl + Agral ™ 90 | 8 + 0.25 |
| NaCl + Agral ™ 90 | 12 + 0.25 |
| NaCl + Citowett ™ | 8 + 0.25 |
| NaCl + Citowett ™ | 12 + 025 |
| KNO₃ | 12 |

Only the 8% and 12% rates were considered in this experiment because it had been observed that there was no efficacy or economic benefit to using the 16% or 20% rates of NaCl. Both NaCl concentrations were applied alone or with each of the three surfactants.

Alone, the 8% concentration of NaCl showed inferior control of ragweed compared with the 12% solution. However, the effects such as drooping 30 minutes after application and complete necrosis 2 days after spraying were similar for the 8% solution with Citowett™ as for the 12% solution applied alone or with either Agral™ 90 or Citowett™. Agral™ 90 also improved the efficacy of the 8% NaCl treatment but the effects were greater when Citowett™ was the surfactant. Both Agral™ 90 and Citowett™ performed similarly when mixed with the 12% solution.

General Conclusions

Salt solutions, and especially NaCl solutions, are effective at ragweed control. If applied alone, a solution having a salt concentration of 12% gives adequate control. Concentrations greater than 20% do not seem to offer superior ragweed control and are not as economical.

Surfactants add to the efficacy of the salt solutions by improving coverage. When a surfactant is used, it is possible to achieve as effective ragweed control with an 8% salt solution as with a 12% solution. In a preferred embodiment, Agral™ 90 and Citowett™ were tested and found to be excellent surfactant options.

It is preferred that the ragweed be fully covered and wetted to run-off by the spray solution. Spray volumes will likely have to be calculated based on plant size and stage as well as whether or not a surfactant is being used. Without a surfactant, more spray volume will be necessary to obtain adequate coverage. KNO₃ is not a viable alternative to NaCl at the 12% rate.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for selective control of ragweed, comprising the step of spraying ragweed to a run-off point with a solution consisting of 8% to 20% weight to volume of NaCl.

2. The method of claim 1 wherein said solution is in combination with at least one adjuvant selected from the group consisting of nonionic or cationic surfactants, mineral oils, mineral oil surfactants, vegetable oils, spreader sticker, wetting agent, and ammonium sulfate.

3. The method of claim 1, wherein the solution consists of 8% to 12% weight to volume of NaCl.

4. The method of claim 3 wherein said solution is in combination with at least one adjuvant selected from the group consisting of nonionic or cationic surfactants, mineral oils, mineral oil surfactants, vegetable oils, spreader sticker, wetting agent, and ammonium sulfate.

5. The method of claim 3 wherein said solution comprises 12% weight to volume of NaCl.

6. The method of claim 5, wherein said solution is in combination with at least one adjuvant selected from the group consisting of nonionic or cationic surfactants, mineral oils, mineral oil surfactants, vegetable oils, spreader sticker, wetting agent, and ammonium sulfate.

* * * * *